US007291478B1

(12) United States Patent
Elashvili

(10) Patent No.: US 7,291,478 B1
(45) Date of Patent: Nov. 6, 2007

(54) RAPID SCREENING AND ANALYSIS OF PRESENT AND POTENTIAL NERVE AGENTS AND THEIR DEGRADATION PRODUCTS

(75) Inventor: Ilya Elashvili, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 33 days.

(21) Appl. No.: 11/094,548

(22) Filed: Mar. 29, 2005

(51) Int. Cl.
*C12Q 1/34* (2006.01)
*C12Q 1/44* (2006.01)
*C12N 9/14* (2006.01)

(52) U.S. Cl. .......................... 435/18; 435/19; 435/195

(58) Field of Classification Search .................... None
See application file for complete search history.

(56) References Cited

U.S. PATENT DOCUMENTS 3,910,763 A * 10/1975 Poziomek et al. .......... 436/104
6,897,032 B1 * 5/2005 Elashvili ..................... 435/18

* cited by examiner

*Primary Examiner*—Jon Weber
*Assistant Examiner*—Paul Martin
(74) *Attorney, Agent, or Firm*—Ulysses John Biffoni

(57) ABSTRACT

Methods are described for detecting organophosphorus compounds in a sample.

14 Claims, No Drawings

RAPID SCREENING AND ANALYSIS OF PRESENT AND POTENTIAL NERVE AGENTS AND THEIR DEGRADATION PRODUCTS

GOVERNMENT INTEREST

The invention described herein may be manufactured, used and licensed by or for the U.S. Government.

FIELD OF THE INVENTION

The present invention relates to chemical agent detection, and more particularly to methods of determining the presence of organophosphorus based compounds.

CROSS-REFERENCE TO RELATED APPLICATIONS

This patent application is related to U.S. patent application Ser. No. 10/131,996, entitled "Method for Detecting G- and V-Agents of Chemical Warfare and Their Degradation Products," filed on Apr. 23, 2002, which is hereby incorporated by reference herein to the extent there is no conflict.

BACKGROUND OF THE INVENTION

Organophosphorus compounds are highly toxic to many organisms including humans. Such compounds including, for example, sarin, cyclosarin, soman, and tabun are also used as nerve agents for chemical warfare applications. These agents are some of the most potent toxic agents and are specific inhibitors of acetylcholinesterase (AChE). These inhibitors induce ACHE poisoning in humans corresponding to the accumulation of acetylcholine at all cholinergic receptor terminals, which results in blockage of neural signal transmissions. These nerve agents are generally classified into G agents (e.g., GD, soman; GB, sarin; and GA, tabun) and V agents (e.g., VX).

The various nerve agents differ in physical properties, for example, VX has a much lower vapor pressure than the G agents. However, the toxicity and main effects of the agents are very similar—inhibition of acetylcholinesterase that results in subsequent breakdown of the normal operation of the autonomic and central nervous systems. Rapid and reliable detection of organophosphorus compounds is of paramount importance to prevent casualties due to exposure to such compounds.

Organophosphorus compounds contain at least one phosphorous atom chemically bonded directly or indirectly to a carbon skeleton. The phosphorous atom may be a member of an organic chain or ring system in which phosphorous is bonded directly to carbon, or phosphorous may be the central atom in a functional group which in turn is bonded to a carbon containing chain or ring. Such functional groups commonly have one or more oxygen atoms or hydroxyl (—OH) groups surrounding the phosphorous atom. These compounds are generally represented by the Formula (I)

$$R_1\text{—O—}\overset{\overset{\displaystyle O}{\|}}{\underset{\underset{\displaystyle X}{|}}{P}}\text{—}R_2 \qquad (I)$$

wherein $R_1$ and $R_2$ are independently selected from organic moieties including aliphatic groups, aromatic groups, and heterocyclic groups, and X is a leaving group which is energetically labile as an anion or a negatively charged group. The phosphorous atom of the compound exhibits the capacity to receive three functional or substituent groups in the form of $R_1$, $R_2$ and X, which enables a range of chemical variants to be produced including previously unknown ones with similar chemical effects.

Recent events involving terrorism around many parts of the world have highlighted the need for devices capable of detecting such dangerous organophosphorus compounds for use by both military and civilian personnel. The need for the reliable determination of these organophosphorus compounds particularly those with cholinesterase inhibiting effects has led to the development of a number of sophisticated methods, mostly involving the use of gas and liquid chromatography and mass spectrometry. Accurate detection and quantification of toxic substances is generally achievable, however at relatively high cost and extended response time. Additionally, the measurement of nerve agents in mixtures with these traditional methods requires cumbersome extraction and manipulation procedures.

Despite this need, the sensitive and chemically specific detection of organophosphorus compounds remains a significant challenge. This is due, in part, to the extreme toxicity of organophosphorus compounds: the median lethal dose for the nerve agent VX is 7 µg per kg of body weight for a normal adult, requiring sensitivity levels in the range of parts per billion.

Current methods for analyzing organophosphorus compounds having nerve agent activity have been limited, particularly with respect to previously unknown organophosphorus nerve agents. Such methods require multi-instrumental investigations, thus necessitating larger sample amounts and extensive time and effort for reliable implementation. Samples obtained from the environment can contain a range of complex organophosphorus compounds generated from biological and industrial sources. The labile nature of such compounds requires a rapid method of analysis.

It would be useful to have a detection mechanism with features, which are applicable to both military and commercial product markets including cost effectiveness, high reliability and capability of identifying organophosphorus compounds. Satisfying these demanding requirements necessitates a novel approach to the measurement of low concentrations of organophosphorus compounds including those previously unknown. There is a further need to provide a rapid, efficient and highly reliable method of detecting, identifying and quantifying known and prospective chemical agent threats specifically organophosphorus based nerve agents and their corresponding degradation products.

SUMMARY OF THE INVENTION

The present invention relates generally to a method of determining the presence of organophosphorus compounds in a sample. The method of the present invention provides a rapid and reliable approach for detecting known and previously unknown organophosphorus compounds. The present invention is designed to generate chemical products from a parent compound that are very stable for use as important markers and biomarkers of such compounds, which may be represented in the form of unique chemical indicators generated by suitable chemical analyzing means. In particular, the method of the present invention involves degrading the organophosphorus compounds using suitable hydrolyzing agents, and analyzing the corresponding products through suitable chemical analyzing means for obtaining a unique profile or fingerprint from the corresponding multiple analytes to identify the organophosphorus compounds that may be present.

The present invention utilizes a combination of alkali and chemical specific enzymatic transformations of the organophosphorus compound to generate three distinct phospho-analytes. This approach produces a unique profile that allows screening and identification of known and potential nerve agents using currently available chemical analyzing techniques such as, for example, gas chromatography in combination with a flame photometric detector (GC-FPD) and phosphorous filter, gas chromatography in combination with the Pulsed Flame Photometric Detector (GC-PFPD), liquid chromatography-mass spectrometry (LC/MS), and the like. The compounds and individual components of these pre-instrumentation derived products can be further interrogated by the existing instrumental methods (e.g., GC-MS, GC-MS/MS) for specific identification.

In one aspect of the present invention, there is provided a method of determining the presence of a compound of Formula (I)

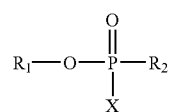

wherein $R_1$ and $R_2$ are independently selected from a group consisting of an organic moiety, and X is a leaving group which is energetically labile as an anion or a negatively charged group, with the proviso that when $R_2$ is methyl and X is fluorine, then $R_1$ is not isopropyl, cyclohexyl or pinacolyl;

when $R_2$ is methyl and X is S-(2-diisopropylaminoethyl), then $R_1$ is not ethyl; and when $R_2$ is methyl and X is S-(2-diethylaminoethyl), then $R_1$ is not i-butyl, in a sample suspected of containing the same, the method comprises the steps of:

treating the sample with a first hydrolyzing agent in amounts sufficient to convert the compound of Formula (I) to a detectable amount of a corresponding compound of Formula (II)

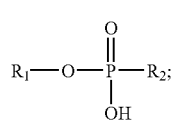

treating the sample with a second hydrolyzing agent in amounts sufficient to convert the compound of Formula (II) to a detectable amount of a corresponding compound of Formula (III)

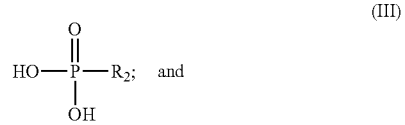

analyzing the sample to determine the presence of the compound of Formula (III) wherein the presence of the compound of Formula (III) indicates the presence of the compound of Formula (I) in the sample.

In another aspect of the present invention, there is provided a method of determining the presence of a compound of Formula (I)

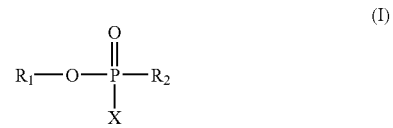

wherein $R_1$ and $R_2$ are independently selected from a group consisting of an organic moiety, and X is a leaving group which is energetically labile as an anion or a negatively charged group, with the proviso that when $R_2$ is methyl and X is fluorine, then $R_1$ is not isopropyl, cyclohexyl or pinacolyl;

when $R_2$ is methyl and X is S-(2-diisopropylaminoethyl), then $R_1$ is not ethyl; and when $R_2$ is methyl and X is S-(2-diethylaminoethyl), then $R_1$ is not i-butyl, in a sample suspected of containing the same, the method comprises the steps of:

analyzing the sample to yield a first chemical indicator corresponding to a specific one of the compound of Formula (I);

treating the sample with a first hydrolyzing agent to yield a compound of Formula (II),

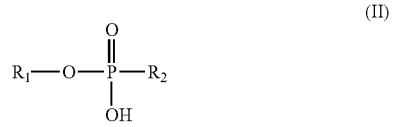

analyzing the first hydrolyzing agent treated sample to yield a second chemical indicator corresponding to a specific one of the compound of Formula (II);

treating the sample with a second hydrolyzing agent to yield a compound of Formula (III),

analyzing the second hydrolyzing agent treated sample to yield a third chemical indicator corresponding to a specific one of the compound of Formula (III); and evaluating at least one of the first, second and third chemical indicators to confirm the presence of the compound of Formula (I) in the sample.

In a particular aspect of the present invention, the first hydrolyzing agent is capable of selectively cleaving the compound of Formula (I) at the P—X bond, and the second hydrolyzing agent is capable of selectively cleaving the compound of Formula (II) at the $R_1$ ester bond.

DETAILED DESCRIPTION OF THE INVENTION

The present invention is directed to a method of determining the presence of an organophosphorus compound in a sample suspected of containing the same. The method of the present invention utilizes a first hydrolyzing agent specific to a parent organophosphorus compound for conversion to an intermediate compound, and a second hydrolyzing agent specific to the intermediate compound for conversion to a final compound. The detection of the final compound and/or the detection of the final compound in combination with the parent and intermediate compounds provide a positive result. In one aspect of the present invention, specific enzymes in combination with alkali compounds are utilized to enhance the scope, speed and reliability necessary to detect and analyze the presence of organophosphorus compounds including those previously unknown. In particular, the method of the present invention utilizes sequential degradation of the compounds and subsequent analysis of the compounds and the corresponding products to generate a specific fingerprint or profile therefrom.

The present invention augments existing chemical warfare agent detection methods and is based on a novel generic method that is predicated by the specificity of organophosphorus hydrolyzing enzymes such as phosphonate ester hydrolase (PEH) to degrade the phosphonate ester products of the compounds. The method can be used for both initial screening and identification purposes with vastly improved efficiency and reliability. The methods of the present invention would be suitable for many applications, both military and civilian. It would be especially well suited for Chemical Weapons Convention (CWC) verification purposes, where the highest degree of reliability is required and both the allotted time and the allocated equipment are very limited. In this regard, the proposed method could be applicable for Domestic Preparedness and Homeland Defense Programs as well.

By making use of the specificity of certain organophosphorus hydrolyzing enzymes including phosphonate ester hydrolase (PEH) alone, or optionally in combination with organophosphorus hydrolase (OPH) and/or organophosphorus acid anhydrolase (OPAA)—the present invention is able to facilitate the identification and quantification of both known and unknown organophosphorus compounds based on phosphonate esters and their degradation phospho-products.

In one embodiment of the present invention, there is provided a method of determining the presence of a compound of Formula (I)

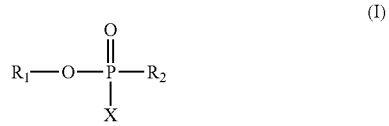

wherein $R_1$ and $R_2$ are independently selected from a group consisting of an organic moiety, and X is a leaving group which is energetically labile as an anion or a negatively charged group, with the proviso that when $R_2$ is methyl and X is fluorine, then $R_1$ is not isopropyl, cyclohexyl or pinacolyl;

when $R_2$ is methyl and X is S-(2-diisopropylaminoethyl), then $R_1$ is not ethyl; and when $R_2$ is methyl and X is S-(2-diethylaminoethyl), then $R_1$ is not i-butyl, in a sample suspected of containing the same, the method comprises the steps of:

treating the sample with a first hydrolyzing agent in amounts sufficient to convert the compound of Formula (I) to a corresponding compound of Formula (II)

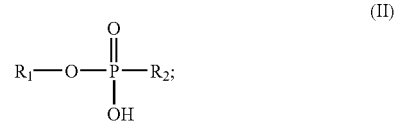

treating the sample with a second hydrolyzing agent in amounts sufficient to convert the compound of Formula (II) to a corresponding compound of Formula (III)

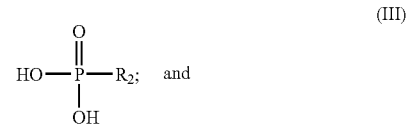

analyzing the sample to determine the presence of the compound of Formula (III) wherein the presence of the compound of Formula (III) indicates the presence of the compound of Formula (I) in the sample.

In another embodiment of the present invention, there is provided a method of determining the presence of a compound of Formula (I)

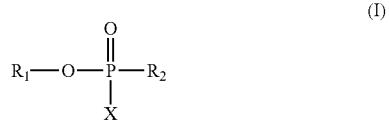

wherein $R_1$ and $R_2$ are independently selected from a group consisting of an organic moiety, and X is a leaving group which is energetically labile as an anion or a negatively charged group, with the proviso that when $R_2$ is methyl and X is fluorine, then $R_1$ is not isopropyl, cyclohexyl or pinacolyl;

when $R_2$ is methyl and X is S-(2-diisopropylaminoethyl), then $R_1$ is not ethyl; and when $R_2$ is methyl and X is S-(2-diethylaminoethyl), then $R_1$ is not i-butyl, in a sample suspected of containing the same, the method comprises the steps of:

analyzing the sample to yield a first chemical indicator corresponding to a specific one of the compound of Formula (I);

treating the sample with a first hydrolyzing agent to yield a compound of Formula (II),

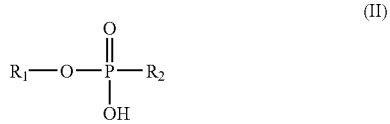

(II)

analyzing the first hydrolyzing agent treated sample to yield a second chemical indicator corresponding to a specific one of the compound of Formula (II);

treating the sample with a second hydrolyzing agent to yield a compound of Formula (III),

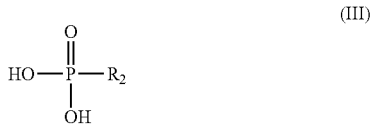

(III)

analyzing the second hydrolyzing agent treated sample to yield a third chemical indicator corresponding to a specific one of the compound of Formula (III); and evaluating at least one of the first, second and third chemical indicators to confirm the presence of the compound of Formula (I) in the sample.

As used herein, the term "organic moiety" refers to a range of aliphatic groups including alkyl, heteroalkyl, heteroalkenyl, heteroalkynyl, cycloalkyl, alkenyl, alkynyl, haloalkyl, alkoxy, and the like, aromatic groups, and heterocyclic groups.

As used herein, the term "aliphatic" refers to a linear, branched, cyclic alkane, alkene, or alkyne. Representative aliphatic groups have from 1 to 36 carbon atoms wherein lower aliphatic groups have from about 1 to 12 carbon atoms and higher aliphatic groups have about 10 to about 24 carbon atoms.

As used herein, the terms "aryl" or "aromatic" refer to an unsaturated cyclic carbon compound with 4n+2 delocalized Tr electrons where n is a non-negative integer. Representative aryl groups include from about 5 to 18 aromatic ring atoms and from about 1 to 3 aromatic rings.

As used herein, the terms "heterocyclic" and "heteroalicyclic" refer to a saturated or unsaturated ring compound having one or more atoms other than carbon in the ring, for example, nitrogen, oxygen or sulfur. Typical heterocyclic groups include heteroaromatic and heteroalicyclic groups that have about a total of 3 to 8 ring atoms and 1 to about 3 fused or separate rings and 1 to about 3 ring heteroatoms such as N, O or S atoms.

The method of the present invention is further useful for determining the presence of the compounds of Formula (I) wherein $R_1$ is independently selected from $CH_3$—, $CH_3CH_2$—, $CH_3CH_2CH_2$—, $(CH_3)_2CH$—, $CH_3CH_2CH_2CH_2$—, $(CH_3)_2CHCH_2$—, $(CH_3)_3CCH$-$(CH_3)_2$—, $C_6H_{11}$, $NO_2C_6H_5$—, and $C_6H_5CH_2$—, and $R_2$ is independently selected from $CH_3$—, $CH_3CH_2$—, $CH_3CH_2CH_2$—, $CH_3CH_2CH_2CH_2$—, $CH_2CHCH_2$—, $C_6H_5$—, $C_6H_5CH_2$—, $CH_3C_6H_5CH_2$—, $CH_2CH$—, and $C_6H_5C(O)$—. The leaving group X can be selected from any moiety that is energetically labile as an anion or a negatively charged group including, but not limited to, a halogen, a cyamide group, and a mercaptan group.

The compounds of Formula (I) are part of a class of organophosphorus compounds referred to as phosphonates. Phosphonates encompass chemical warfare agents including extremely toxic cholinesterase inhibitors. Each of the compounds possesses a phosphonate ester in the structure wherein $R_1$ is bonded to the oxygen atom via a carbon atom, and $R_2$ is bonded to the phosphor atom via a carbon atom. The phosphor atom of the phosphonate ester is pentavalent, which facilitates substitution at three positions $R_1$, $R_2$, and X, representing a "tri-substituted compound." The three positions on the phosphor atom can accept a number of possible groups for attachment thereto. This enables large variations of known compounds and previously unknown ones to be generated. Thus, the present invention provides a method of detecting, identifying, and quantifying the presence of chemical warfare agents that contain organophosphorus compounds. The method is useful to detect and analyze not only known organophosphorus compounds, but also presently unknown/unclassified organophosphorus compounds.

The method of the present invention is useful for detecting the presence of organophosphorus compounds of Formula (I) including, but not limited to, dimethyl methylphosphonate, dibutyl methylphosphonate, diethyl vinylphosphonate, diethyl benzylphosphonate, diethyl benzoylphosphonate, diethyl allylphosphonate, diethyl ethylphosphonate, dimethyl phenylphosphonate, diethyl-4-methylbenzylphosphonate, and combinations thereof.

Applicants have observed that by selectively hydrolyzing the compound to yield specific products via a two step process, a unique fingerprint or profile of a compound of Formula (I) can be generated for accurate identification. The products can be detected in the sample using known chemical analysis methods to generate the profile. Referring to Scheme 1, prior to treatment, a sample is chemically analyzed to make a preliminary reading to generate a first chemical indicator. The sample is treated with a first hydrolyzing agent to remove the leaving group from the compound of Formula (I) that may be present. The first hydrolyzing agent may be selected from alkaline compounds such as sodium hydroxide, potassium hydroxide and the like and enzymatic agents capable of cleaving the P—X bond of the compound of Formula (I) including phosphoric triester hydrolase enzymes such as organophosphorus hydrolase. This results in a hydrolytic removal of the leaving group (X), thus yielding a compound of Formula (II) (i.e., $R_1$ phosphonate ester), a di-substituted phosphonate. The treated sample is chemically analyzed to make a reading of the product to generate a second chemical indicator.

Thereafter, the sample is treated with a second hydrolyzing agent to hydrolyze the $R_1$-ester bond of the compound of Formula (II) to yield a corresponding compound of Formula (III) (i.e., $R_2$ phosphonic acid), a mono-substituted phosphonate. The second hydrolyzing agent may be selected from any enzymatic agent capable of selectively cleaving the $R_1$—O bond of the compound of Formula (II). The treated sample is again chemically analyzed to make a reading to generate a third chemical indicator. The second hydrolyzing agent is selected from enzymes such as phosphonate ester hydrolase to perform enzyme mediated hydrolysis. As described above, the differences in the properties of the parent compound and the products can be used to generate a unique profile represented by the generated chemical indicators. For example, different volatility characteristics of the indicator compounds (I, II and III) results in the distinct retention indices and provide useful chemical indicators for identifying the parent compound.

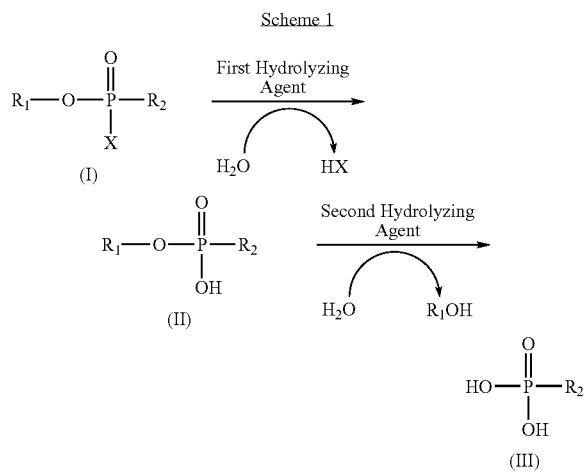

The present invention provides a simple method for quickly screening incoming samples for the presence of known organophosphorus compounds such as GB, GD, GF, VX, and Russian VX agents, as well as previously unknown organophosphorus compounds. Addition of a first hydrolyzing agent selected from an alkaline compound or an enzymatic agent capable of selectively treating the tri-substituted compound of Formula (I) to each sample enables the conversion of the organophosphorus compounds to a di-substituted phosphonate ester product (i.e., compound of Formula (II)) prior to instrumental analysis. The labile character of the organophosphorus compounds makes it likely that post-exposure samples would already contain considerable amounts of the highly stable phosphonate ester degradation products. This approach allows these degradation phosphonate ester products to be readily identifiable, and thus provides important biomarkers and markers for both known and previously unknown organophosphorus compounds that are based on phosphonate esters. In addition, with all of the embodiments of the present invention it is possible to detect, identify, and quantify other phosphonate ester degradation products besides methylphosphonate, including compounds having, for example, an alkyl or aryl substitution to the $R_2$ group in the above-described Formula (I) (for example, ethylphosphonate, or phenylphosphonate).

In the present invention, the first hydrolyzing agent may be selected from an alkaline compound such as sodium hydroxide, ammonium hydroxide, potassium hydroxide, alkaline pH buffer, and the like, and combinations thereof, a tri-substituted organophosphorus hydrolyzing enzymatic agent capable of selectively hydrolyzing tri-substituted organophosphorus compounds (i.e., compounds of Formula (I)) particularly at the P—X bond, such as, for example, organophosphorus hydrolase, organophosphorus acid anhydrolase, diisopropyl fluorophosphatase (DFPase), paraoxonase, parathion hydrolase, and combinations thereof.

The second hydrolyzing agent may be selected from a di-substituted organophosphorus hydrolyzing enzymatic agent capable of selectively hydrolyzing di-substituted organophosphorus compounds (i.e., compounds of Formula (II)) particularly at the $R_1$ ester bond.

In a further embodiment of the present invention, there is provided a method includes the steps of:

(a) contacting a liquid sample suspected of containing organophosphorus compounds, and mixtures thereof, with a sufficient amount of a first hydrolyzing agent selected from an alkaline compound such as, for example, sodium hydroxide, potassium hydroxide, ammonium hydroxide, and the like, including a high pH buffer, and a specific hydrolyzing enzyme such as, for example, organophosphorus hydrolase (OPH), or organophosphorus acid anhydrolase (OPM) and the like, and combinations thereof, and time, to convert the organophosphorus compound to at least a detectable amount of its corresponding phosphonate ester, (b) neutralizing the sample of step (a) using known protocols including, but not limited to, titration with hydrochloric acid, and/or by adding a buffer to bring the resulting solution to the desired pH, (c) treating the sample of step (b) with a sufficient amount of an organophosphorus specific hydrolyzing enzyme such as, for example, phosphonate ester hydrolase (PEH), and time, to convert the phosphonate ester to at least a detectable amount of its corresponding phosphonate, and (d) detecting the presence of phosphonate such as methylphosphonate, which presence is indicative of organophosphorus compounds. Preferably, the degradation product phosphonate may be detected using liquid or gas chromatography, mass spectrometry, flame photometric detector and phosphorus filter, or any combination of these techniques.

Preferably, the amount of the first hydrolyzing agent in the form of a tri-substituted organophosphorus hydrolyzing enzymatic agent such as organophosphorus hydrolase is at least about 25 DFP units per ml. Preferably, the amount of organophosphorus acid anhydrolase used is at least about 25 DFP units per ml. It is noted that one EMPA unit will hydrolyze 1.0 micromole of ethyl methylphosphonate (EMPA) per minute. Similarly, one DFP unit will hydrolyze 1.0 micromole of diisopropyl fluorophosphate (DFP) per minute.

Preferably, the amount of the second hydrolyzing agent in the form of a di-substituted organophosphorus hydrolyzing enzymatic agent such as phosphonate ester hydrolase is at least about 0.5 EMPA units per ml. It is noted that one EMPA unit will hydrolyze 1.0 micromole of ethyl methylphosphonate (EMPA) per minute.

In one particular embodiment of the present invention, the method comprises employment of an alkaline compound and PEH. The only enzyme employed in this particular method is PEH. For instance, four aliquots of the sample are analyzed as follows: one aliquot contains only the untreated sample; a second aliquot contains the sample plus alkali, so that this sample solution is neutralized (e.g., treated with 1/10 volume of 10 N NaOH for 1 hour and neutralized with 1/10 volume of 10 N acid); a third aliquot contains only PEH; and a fourth aliquot contains a part of the sample contained in the second aliquot following neutralization, plus PEH. After allowing sufficient time for the enzymes to hydrolyze all or most of the substrates in a buffered aqueous solution, the first aliquot containing only the untreated sample may be analyzed by gas chromatography in two capacities-without derivatization and after being derivatized. The other three aliquots may be analyzed by gas chromatography after derivatization and the results are then compared. The peaks from the gas chromatography analysis will indicate additional specificity about the particular nerve agent in the sample.

The present invention contemplates a gas chromatography-flame photometric detector/mass spectrometry (GC-FPD/MS) methodology that would facilitate the reliability and speed for detection, identification, and quantification of known and unknown organophosphorus compounds with phosphonate ester moieties and their degraded phospho-products.

The sample to be tested is preferably in the form of a solution. In one aspect of the present invention, the solution is obtained by wiping a suspected surface with a polyester or similar type wipe or cloth and thereafter extracting the materials present on the wipe with a aqueous buffer solution such as 5 mM Bis Tris Propane, pH 7.0. Alternatively, a soil sample can be eluted to obtain the liquid sample for analysis. A still further aspect includes treating an aliquot of an organic solvent including a sample suspected of containing the organophosphorus compound as an analyte with an alkali for a sufficient time (such as, for instance, about one hour) and subsequently evaporating the organic solvent and neutralizing the remaining aqueous solution with an acid to obtain hydrolyzed derivative of the organophosphorus compound as an analyte believed to be therein.

In another embodiment of the invention there is provided kits for detecting the presence of chemical warfare agents that contain organophosphorus compounds, precursors of chemical warfare agents, and degradation products thereof. One such kit includes, packaged in association:

(a) phosphonate ester hydrolase (preferably at least about 0.5 EMPA units), an alkali, and a neutralizing agent, and (b) a detection device for detecting the presence of the compound of Formula (III), which presence is indicative of chemical warfare agents that contain organophosphorus compounds. The detection device may be further calibrated to detect the compounds of Formula (I) and (II).

Another such kit includes, packaged in association:

(a) phosphonate ester hydrolase (preferably at least about 0.5 EMPA units), optional organophosphorus hydrolase (preferably at least about 25 DFP units), and optional organophosphorus acid anhydrolase (preferably at least about 25 DFP units), and (b) a detection device for detecting the presence of the compound of Formula (III), which presence is indicative of chemical warfare agents that contain organophosphorus compounds. The detection device may be further calibrated to detect the compounds of Formula (I) and (II).

Advantages of these kits, and indeed all of the embodiments of the present invention, are its tremendous reliability utilizing the specificity of these enzymes.

When desirable, a chromogenic detector reagent may be used with the compositions, methods of detection and kits of the present invention.

The PEH enzymes may be obtained from $B.$ $caryophilli$, such as strain PG2982. Bacteria cells PG2982 were deposited on Mar. 5, 2002 with the ATCC, P.O. Box 1549, Manassas, Va. 20108 under Accession No. PTA-4116. The PEH enzymes may be produced and purified using well-established methods (e.g., gel-filtration, ion-exchange, hydroxyapatite, and hydrophobic interaction chromatographies). Further details on the producing PEH can be found in U.S. Pat. No. 6,838,277, the content of which is incorporated herein by reference. Substrate specificities for the purified PEH may be ascertained using techniques known in the art for selected alkyl-alkyl-, alkyl-aryl-, aryl-alkyl-, and aryl-aryl-phosphonate esters and pesticide degradation products. The reaction rate kinetics and the optimal reaction conditions may also be ascertained using techniques known in the art. For routine kinetics, GC-FPD may be used for the agents and silylated derivatives of the analytes. The enzymes may be produced, purified, freeze-dried, immobilized, and encapsulated or otherwise stabilized. GC-FPD/MS may be used for database and agent identification.

Two different assay methods may be used for monitoring PEH activity. For screening large numbers of samples (e.g., chromatographic effluents), chromogenic substrate may be used in calorimetric assays. Samples showing activity for the chromogenic substrate may be evaluated further with selected hydrolyzed-agent substrates using GC-FPD for silylated derivatives of the analytes. GC-FPD analysis may also be used to study the enzymatic hydrolysis of agents. For VX and R-VX degradation studies, in addition to the GC-FPD analysis, Ellman's reagent/DTNB calorimetric method may be used.

Methods for obtaining OPH are described in U.S. Pat. No. 5,589,386, the content of which is incorporated herein by reference. Methods for obtaining OPAA are described in U.S. Pat. No. 5,928,927 and U.S. Pat. No. 6,080,566, each of which is incorporated herein by reference.

The present invention also contemplates an analytical database cataloguing known and previously unknown organophosphorus compounds and their products including phosphonates and phosphonate esters. For instance, a modest database consisting of approximately 25-60 compounds may be created without great expense and effort.

EXAMPLE

Production of Phosphonate Ester Hydrolase

A culture of $Burkholderia$ $caryophilli$ PG2982 was grown in modified MOPS minimal media. The modified MOPS minimal media was formulated to contain 7.0 g MOPS (morpholinopropanesulfonic acid), 2.4 g NaCl, 0.6 g Tricine, 0.43 g $NH_4Cl$, 85 mg $MgCl_2.6H_2O$, 40 g $K_2SO_4$, 8.3-mg Thiamine, 1.9 mg $FeSO_4.H_2O$, 1.67 ml Salts (6.0 g $MgCO_4.7H_2O$, 3.0 g nitrilotriacetic acid, 1.0 g NaCl, 1.0 g $MnSO_4.H_2O$, 0.5 g $FeSO_4.7H_2O$, 0.1 g $CaCl_2$ $2H_2O$, 0.1 g $CoCl_2.6H_2O$, 0.1 g $ZnSO_4.7H_2O$, 20 mg $H_3BO_3$, 10 mg $Na_2MoO_4.2H_2O$, 10 mg $CuSO_4$ per liter), 4.2 ml 20% glucose, 2.3 ml 40% sodium citrate, 2.3 ml 40% potassium gluconate with final pH adjusted to 7.4 with KOH, plus 0.3 mM final concentration of methyl methylphosphonate (obtained from dimethyl methylphosphonate through alkali hydrolysis, and subsequent titration to neutral pH) used as the sole phosphorous source.

A nutrient agar plate was streaked with $B.$ $caryophilli$ and incubated at about 30° C. for about 16-24 hours. A single colony was selected for initiating a seed culture in modified MOPS minimal media and grown for about 24 hours at about 30° C. using a shaking incubator set at 200 rpm. 8.3 ml of the seed culture, O.D. 600 nm ~1.6, was used to initiate 2.4 L cultures in 6 L flasks and incubated for about 48 hours. Cells were harvested by centrifugation at about 6174×g, 4° C. for about 15 minutes. The cells were washed with 15 ml 0.2 M NaCl per 400 ml initial culture, and pelleted at 17,640×g. Pellets were frozen at −80° C. prior to resuspension in 100 mM Tris-Cl pH 8.0, 100 mM KCl, 2 mM DTT and lysed using a French press with a 1" diameter pressure cell three times at pressures greater than 16,000 psi. Cell debris was pelleted at 24,000×g at 4° C. for about 30 minutes. The resulting crude extract was stored at about −80° C. The chromogenic substrate p-nitrophenyl phenyl phosphonate was used to assay for phosphonate ester hydrolase activity during purification. Unless otherwise noted, all chemicals were obtained from Sigma Chemical Co. (St. Louis, Mo.).

Chromogenic Activity Assay

The PEH extract in the amount of 2-10 μl was mixed with an assay mix (2 mM p-nitrophenyl phenyl phosphonate, 20 mM bis-tris propane, pH 8.5, 0.5 mM $MnCl_2$) to a total volume of 1 ml. Absorbance was monitored at 405 nm at 30 second intervals at about 22° C. for about 4 minutes using a Beckman Du-640 spectrometer. A molar extinction coefficient of about $1.74 \times 10^4$ was determined for the p-nitrophenol product.

Partially Purified PEH Extract

It is noted that all purification steps were performed at 0-4° C. and all solutions used were ice-cold.

The crude extract was diluted with 2 mM DTT in a ratio amount of 1:3. The mixture was loaded onto a DEAE Sepharose FF (Pharmacia) 2.5×15 cm column equilibrated with 20 mM Tris-Cl pH 8.0, 2 mM DTT. The column washed with 225 ml 20 mM Tris-Cl pH 8.0, 2 mM DTT followed by 280 ml 100 mM KCl, 100 mM Tris-Cl pH 8.0, 2 mM DTT. PEH was eluted with 200 ml 270 mM KCl, 100 mM Tris-Cl pH 8.0, 100 mM KCl, 2 mM DTT, collected in 20 ml fractions.

The active fractions from the DEAE step gradient were pooled and precipitated with $(NH_4)_2SO_4$ 80% saturation. The precipitated protein was collected by centrifugation at 25,000×g for about 30 minutes and the pellet was resuspended in a minimal volume of 100 mM KCl, 100 mM Tris-Cl pH 8.0, 2 mM DTT and frozen at about −80° C. until use.

Phosphonate Ester Compounds

Samples of nerve agents consisting of GB (sarin), GD (soman), GF (cyclosarin), VX, and Russian VX in the amount of about 2 g were alkali hydrolyzed with 40 ml 1.0 N NaOH at about 22° C. for seven days after which the solutions were titrated to neutral pH with HCl, the concentration adjusted to 28.5 mM with deionized water, and subsequently sterilized by filtration through 0.2 micron filter. The hydrolysis of nine commercially obtained dialkyl alkylphosphonates including dimethyl methylphosphonate, dibutyl methylphosphonate, diethyl vinylphosphonate, diethyl benzylphosphonate, diethyl benzylphosphonate, diethyl benzoylphosphonate, diethyl allylphosphonate, diethyl ethylphosphonate, dimethyl phenylphosphonate, and diethyl-4-methylbenzylphosphonate were conducted similarly.

The hydrolyzed nerve agents and hydrolyzed dialkyl alkylphosphonates were tested for their ability to be degraded by the ammonium sulfate precipitated partially purified PEH extract. For each hydrolyzed nerve agent, a 60 μl reaction mixture containing 50 mM BTP pH 9.0, 1 mM $MnCl_2$, 10 mM hydrolyzed nerve agent or hydrolyzed dialkyl alkylphosphonates, was prepared and mixed with 2 μl of PEH extract. The mixture was incubated at about 30° C. At predetermined time intervals, a 10 μl aliquot was drawn from the reaction mixture and added to 150 μl methanol to quench the reaction. The mixture was dried in Speedvac (Saveant, Albertville, Minn.), and derivatized with 50 μl N,O-bis(trimethylsilyl)trifluoroacetamide with 1% trimethylchlorosilane (BSTFA-TMS)(Pierce, Rockford, Ill.) at 10° C. for about 20 minutes. After derivatization, 150 μl acetonitrile was added to the sample, vortexed and transferred to microvial inserts. 1 μl of the sample was drawn for analysis of the organophosphorus compounds using an Agilent 6890 GC-FPD apparatus equipped with an autoinjector and a phosphorous filter on ZB-5 column (30 m×0.32 ID, 0.25 μm filament thickness) (Zebron, Torrance, Calif.). Helium was used as the carrier gas. The GC-FPD apparatus was set with a front inlet pressure of about 8.93 psi, inlet temperature of about 250° C., initial oven temperature of 100° C. ramped to 130° C. at a rate of 10° C./min, then to 280° C. at a rate of 15° C./min and maintained at 280° C. for 3 minutes.

A series of phosphonate ester compounds were obtained from Queens College of CUNY in New York for this experiment. Although the supplier indicated the samples to be pure based on their results of 31P nuclear magnetic resonance analysis, our examination on GC-FPD and on HPLC with Dionex ED50 conductivity detector (Sunnyvale, Calif.) showed the presence of several compounds in some of the samples.

Results and Discussion

The nerve agent test samples were treated with alkaline compounds followed by degradation with PEH as shown in Table 1. All the nerve agent alkaline hydrolyzed compounds (h-Agents) were degraded to methylphosphonic acid (MPA, retention time 4.39 minutes). Gas chromatography in combination with a flame photometric detector equipped with a phosphorous filter was used for analyzing the progress of the hydrolysis reactions. Analysis was made of the samples at times 0 h, ½ h, 1 h, 3 h and 19 h, and analysis of the control was also made.

Gas chromatography and a flame photometric detector having a phosphorous filter were used to analyze the dialkyl alkylphosphonate compounds and their trimethyl silylated (TMS) products. Each step of the alkali hydrolysis and subsequent enzymatic degradation was monitored by GC-FPD. All the alkali hydrolyzed compounds were transformed to alkylphosphonic acid. By hydrolyzing each nerve agent and the dialkyl alkylphosphonate compounds to their intermediates and final products, two additional analytes are now available for analysis. Moreover, the second degradation step allows for increased confidence predicated by the specificity of enzymatic degradation.

Gas chromatography and a flame photometric detector having a phosphorous filter were used to analyze the synthetic alkyl alkylphosphonate compounds and their trimethyl silylated (TMS) products. Using the present invention Applicants were able to develop a retention time database for the silylated alkyl alkylphosphonates and their products via use of GC-FPD as shown in Table 2. The primary advantage of this methodology is the potential to detect novel threat agents due to the specificity of the hydrolyzing enzyme to phosphonate compounds. The retention times ($t_r$) of the compounds and their degradation products are listed in Table 2.

TABLE 1

Retention time ($t_r$) values of nerve agents and their silylated products

| | $t_r$ Values (ca. min.) | | |
|---|---|---|---|
| Agent Name | Agent | h-Agent | MPA |
| GB | 4.9 | 4.0 | 4.4 |
| GD | 7.5 | 6.3 | 4.4 |
| GF | 9.2 | 7.7 | 4.4 |
| VX | 9.9 | 3.7 | 4.4 |
| R-VX | 9.7 | 4.7 | 4.4 |

The hydrolysis of the compounds to their intermediates and products makes available 3 analytes per agent for interrogation. In addition, the PEH degradation step enhances the confidence predicated by the specificity of enzymatic degradation and the distinctiveness of the retention indices. Using this method allows a retention time database to be generated for the agent and its silylated products for future identification reference as shown in Table 1.

The method of the present invention is especially suited for detecting previously unknown threat agents composed of organophosphorus compounds. Alkaline hydrolysis is believed to exhibit reactivity over a wider range of organophosphorus compounds than current organophosphorus hydrolyzing enzymes. Thus, it is important to demonstrate the ability of alkaline compounds to hydrolyze a range of organophosphorus compounds to the corresponding phosphonate esters.

In addition to the five known nerve agents, nine commercially available dialkyl alkylphosphonates including dimethyl methylphosphonate, dibutyl methylphosphonate, diethyl vinylphosphonate, diethyl benzylphosphonate, diethyl benzoylphosphonate, diethyl allylphosphonate, diethyl ethylphosphonate, dimethyl phenylphosphonate, and diethyl-4-methylbenzylphosphonate were converted to their corresponding monoalkyl alkylphosphonates via alkali hydrolysis treatment. These dialkyl alkylphosphonates exhibit substantially stronger ester bonds than the leaving groups of the five known nerve agents and those that are anticipated in prospective nerve agents, since the toxicity is contingent on the ease of removal of the leaving group. This demonstrates the ability of the alkaline compounds to effectively hydrolyze both current and potential organophosphorus compounds into phosphonate esters.

A second consideration of the methods of the present invention is the ability of PEH to hydrolyze a broad range of phosphonate esters. PEH was tested for its ability to degrade broad range of alkyl and aryl esters of phosphonates. Applicants have found that in addition to alkali-treated products of GB, GD, GF, VX, and Russian VX nerve agents, PEH effectively degraded all of the phosphonate esters tested. All 26 synthetic phosphonate esters listed in Table 2 were degraded by PEH. It is noted that the discrepancies of retention time values between Table 1 and Table 2 are due to a slight difference in the lengths of GC columns that were used in different experiments.

TABLE 2

PEH effectively degraded phosphonate esters for an easy presumptive identification

| Phosphonate Ester | Degraded by PEH | $t_r$ (TMS derivatives) Substrate | Product |
|---|---|---|---|
| Ethyl methylphosphonate | YES | 4.2 | 4.7 |
| Isopropyl methylphosphonate | YES | 4.4 | 4.7 |
| Cyclohexyl methylphosphonate | YES | 8.2 | 4.7 |
| Isobutyl methylphosphonate | YES | 5.5 | 4.7 |
| Butyl methylphosphonate | YES | 5.9 | 4.7 |
| Pinacolyl methylphosphonate | YES | 6.5 | 4.7 |
| Methyl methylphosphonate | YES | 3.7 | 4.7 |
| p-Nitrophenyl methylphosphonate | YES | 11.8 | 4.7 |
| Ethyl ethylphosphonate | YES | 4.9 | 5.5 |
| Benzyl phenylphosphonate | YES | 13.1 | 8.9 |
| Cetyl phenylphosphonate | YES | 8.7 | 8.9 |
| Cyclohexyl phenylphosphonate | YES | 12.2 | 8.9 |
| Methyl phenylphosphonate | YES | 8.3 | 8.9 |
| p-Nitrophenyl phenylphosphonate | YES | 15.8 | 8.9 |
| Pinacolyl phenylphosphonate | YES | 10.5 | 8.9 |
| Propyl phenylphosphonate | YES | 8.7 | 8.9 |
| Benzyl propylphosphonate | YES | 10.6 | 6.2 |
| Ethyl propylphosphonate | YES | 5.6 | 6.2 |
| Methyl propylphosphonate | YES | 5.1 | 6.2 |
| Isopropyl allylphosphonate | YES | 6.0 | 6.2 |
| Ethyl allylphosphonate | YES | 5.8 | 6.2 |
| Ethyl benzylphosphonate | YES | 5.6 | 6.1 |
| Isopropyl benzylphosphonate | YES | 5.8 | 6.1 |
| Butyl butylphosphonate | YES | 8.2 | 7.0 |
| Ethyl vinylphosphonate | YES | 4.7 | 5.2 |
| Ethyl benzoylphosphonate | YES | 9.6 | 9.9 |

Applicants have further observed that although PEH effectively degraded alkali-treated products of compounds of Formula (I) and GB, GD, GF, VX, and Russian VX nerve agents, but not the products of similarly treated diisopropyl fluorophosphate (DFP) and three organophosphorus pesticides tested: Malathion, Monocrotophos, and Diazinon. This demonstrated that the PEH enzyme exhibits selective degradation of phosphonate ester bonds that are present in compounds of Formula (I) and the chemical nerve agents, while remaining ineffective against 1- and 2-carbon alkyl ester bonds of phosphates, diisopropyl phosphate, and thiophosphates that are commonly found in pesticides. This demonstrates that PEH can hydrolyze a broad range of organophosphorus compounds of chemical warfare for enabling identification including previously unknown compounds in the present invention, while excluding environmental contaminants including pesticides to avoid false positives.

The present invention facilitates screening for novel variants of known chemical warfare agents including GB, GD, GF, VX, and Russian VX nerve agents in a dependable, rapid and accurate manner. For example, an organophosphorus nerve agent simulant dimethyl methylphosphonate was tested using the method of the present invention. Alkali treatment degrades dimethyl methylphosphonate ($t_r$=2.92 min) to methyl methylphosphonate ester ($t_r$=3.70) as measured by GC-FPD. The ester was subsequently degraded to methyl phosphonic acid ($t_r$=4.72 min) by PEH. The corresponding shift in retention times provides good chemical indicators and enhances greater confidence in the identification peaks of interest. The use of alkali degradation treatment is routinely employed for the analysis of known nerve agents. The introduction of the additional PEH treatment as envisioned in this invention provides a quick screening tool to identify potential nerve agent or its product from other possible phospho-product contaminants present in the sample for a more detailed analysis using for, example, GC/MS/MS. The use of the chemical indicators in the form of specific retention time ($t_r$) values associated with each treatment step (i.e., alkali treatment and PEH treatment) and a database of retention time values for various organophosphorus compounds and their products provides the capability to identify compounds of interest with high degree of reliability.

In addition to providing a suitable database screening process, the present invention provides ease in identifying crucial identification peaks in complex matrices. The use of GC-FPD with a phosphorous filter enables very low detection limits for phosphorous compounds, while greatly reducing background noise, thereby allowing focus on specific phosphorous compounds. The use of the chemical indicators in the form of specific retention time ($t_r$) values associated with each treatment step (i.e., alkali treatment and PEH treatment) and a database of retention time values for various organophosphorus compounds and their products provides the capability to presumptively identify individual compounds of interest without further instrumental analysis. Subsequent instrumental analysis would only be used for confirmation purposes. Some of the synthetic phosphonate esters were contaminated with unknown phosphorous compounds. The present invention allowed easy identification of the synthetic phosphonate ester peak by the corresponding shifts during PEH enzyme treatment. Individual phosphonate esters were presumptively identified using the specific retention time values before and after treatments. The identities of synthetic phosphonate esters were confirmed by GC/MS. It should be noted, that if PEH treatment of a chemical results in the retention time change on GC-FPD after silylation, the unknown chemical can be presumptively identified as a phosphonate ester compound even in the absence of the database parameters; database is needed only for presumptive identification of the individual phosphonate ester.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A method of determining the presence of a compound of Formula (I)

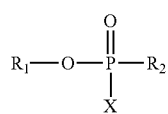

(I)

wherein $R_1$ and $R_2$ are independently selected from a group consisting of organic moieties, and X is a leaving group which is energetically labile as an anion or a negatively charged group, with the proviso that
  when $R_2$ is methyl and X is fluorine, then $R_1$ is not isopropyl, cyclohexyl or pinacolyl;
  when $R_2$ is methyl and X is S-(2-diisopropylaminoethyl), then $R_1$ is not ethyl; and
  when $R_2$ is methyl and X is S-(2-diethylaminoethyl), then $R_1$ is not i-butyl,
in a sample suspected of containing the same, said method comprising the steps of:
  treating the sample with a first hydrolyzing agent, wherein said first hydrolyzing agent is selected from a group consisting of an alkaline compound, a tri-substituted organophosphorus hydrolyzing enzymatic agent and combinations thereof, in amounts sufficient to convert the compound of Formula (I) to a detectable amount of corresponding compound of Formula (II)

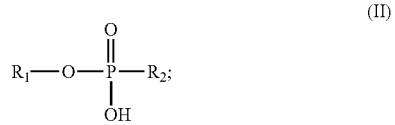

(II)

treating the sample with a second hydrolyzing agent, wherein the second hydrolyzing agent is a di-substituted organophosphorus hydrolyzing enzymatic agent, in amounts sufficient to convert the compound of Formula (II) to a detectable amount of corresponding compound of Formula (III)

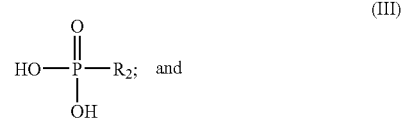

(III)

analyzing the sample to determine the presence of the compound of Formula (III) wherein the presence of the compound of Formula (III) indicates the presence of the compound of Formula (I) in the sample.

2. The method of claim 1 wherein the organic moiety is selected from the group consisting of an aliphatic group, an aromatic group, and a heterocyclic group.

3. The method of claim 2 wherein $R_1$ and $R_2$ are independently selected from a group consisting of an alkyl group, an acyl group, a cycloalkyl group, and an aromatic group.

4. The method of claim 3 wherein $R_1$ is selected from the group consisting of methyl, ethyl, propyl, i-propyl, butyl, i-butyl, pinacolyl, cyclohexyl, nitrophenyl, and benzyl.

5. The method of claim 3 wherein $R_2$ is selected from the group consisting of methyl, ethyl, propyl, butyl, allyl, phenyl, benzyl, methylbenzyl, and benzoyl.

6. The method of claim 1 wherein X is selected from the group consisting of a halogen, a cyamide group and a mercaptan group.

7. The method of claim 1 wherein the compound of Formula (I) is selected from the group consisting of dimethyl methylphosphonate, dibutyl methylphosphonate, diethyl vinylphosphonate, diethyl benzylphosphonate, diethyl benzoylphosphonate, diethyl allylphosphonate, diethyl ethylphosphonate, dimethyl phenylphosphonate, and diethyl-4-methylbenzylphosphonate.

8. The method of claim 1 wherein the alkaline compound is selected from the group consisting of sodium hydroxide, ammonium hydroxide, potassium hydroxide, alkaline pH solution and the like, and combinations thereof.

9. The method of claim 1 wherein the tri-substituted organophosphorus hydrolyzing enzymatic agent is selected from the group consisting of organophosphorus hydrolase, organophosphorus acid anhydrolase, diisopropyl fluorophosphatase (DFPase), paraoxonase, parathion hydrolase, and combinations thereof.

10. The method of claim 1 wherein the di-substituted organophosphorus hydrolyzing agent is selected from a group consisting of a phosphonate ester hydrolase, and combinations thereof.

11. The method of claim 1 further comprising the step of analyzing the untreated sample with Gas-Chromatography-Flame Photometric Detection (GC-FPD) or GC-MS to generate a first chemical indicator corresponding to the organophosphorus compound.

12. The method of claim 11 further comprising the step of analyzing the, sample treated with the first hydrolyzing agent with GC-FPD or GC-MS to generate a second chemical indicator corresponding to the phosphonate ester compound.

13. The method of claim 12 further comprising the step of analyzing the sample treated with the second hydrolyzing agent with GC-FPD or GC-MS to generate a third chemical indicator corresponding to the phosphonate compound.

14. The method of claim 13 further comprising the step of evaluating at least one of the first, second and third chemical indicators to confirm the presence of the organophosphorus compound in the sample.

* * * * *